United States Patent [19] [11] 4,349,540
D'Hinterland et al. [45] Sep. 14, 1982

[54] PROCESS FOR PREPARING VACCINES BASED ON ANTIGENIC RIBOSOMAL FRACTIONS

[75] Inventors: Lucien D. D'Hinterland, Castres; Hubert Serre, Mazamet; Gerard Normier, Castres, all of France

[73] Assignee: Pierre Fabre S.A., France

[21] Appl. No.: 228,823

[22] Filed: Jan. 26, 1981

Related U.S. Application Data

[63] Continuation of Ser. No. 36,125, May 4, 1979, abandoned, which is a continuation-in-part of Ser. No. 776,035, Mar. 9, 1977, abandoned, which is a continuation-in-part of Ser. No. 531,011, Dec. 9, 1974, abandoned.

[30] Foreign Application Priority Data

Dec. 10, 1973 [FR] France .................................. 73 43957

[51] Int. Cl.³ .................. A61K 39/102; A61K 39/09; A61K 39/02
[52] U.S. Cl. ..................................................... 424/92
[58] Field of Search ......................................... 424/92

[56] References Cited

U.S. PATENT DOCUMENTS 3,855,197 12/1974 Hirsch et al. ..................... 424/92 X
4,001,395 1/1977 Jolles et al. ............................ 424/92
4,042,678 8/1977 Ciorbaru et al. ................. 424/92 X

FOREIGN PATENT DOCUMENTS 2613943 10/1976 Fed. Rep. of Germany ........ 424/92

OTHER PUBLICATIONS

Chemical Abstracts, 79:76828c, (1973), [Friedman, H., Ann. N.Y., *Acad. Sci.*, 1973, 207, 178–199].
Chemical Abstracts, 78:41367d, (1973), [Birnschein, E., *Zentra L. Bakteriol., Parasitenk., Infectionskr. Hyg.*, Abt. 1, Orig., Reime A, 1972, 222 (3), 314–3259.
Chemical Abstracts, 85:198156b, (1976), [OLS 2,613,943, 10/14/76].

*Primary Examiner*—Richard A. Schwartz
*Attorney, Agent, or Firm*—Stevens, Davis, Miller & Mosher

[57] ABSTRACT

Vaccines which comprise in association the ribosomal fraction extracted from the bacterias against which a protection is wanted, and the peptidoglycanes extracted from the membranes of at least one of the bacteria previously used.

5 Claims, No Drawings

PROCESS FOR PREPARING VACCINES BASED ON ANTIGENIC RIBOSOMAL FRACTIONS

This application is a continuation of application Ser. No. 36,125, filed May 4, 1979, now abandoned, which is a continuation-in-part of application Ser. No. 776,035, filed Mar. 9, 1977, now abandoned, which was a continuation-in-part of application Ser. No. 531,011, filed Dec. 9, 1974, now abandoned.

BACKGROUND OF THE INVENTION

Conventional vaccines are based on microbial germs which are either dead or have been attenuated by various physico-chemical treatments. Although effective, these vaccines do not have the same antigenic power as the living germs, with the result that there is a considerable loss of antigenic activity during preparation of the vaccines.

It is known that the antigenic power of certain germs is associated with the ribosomes of the microbial cells, and that the antigenic activity of these ribosomal fractions is only developed in the presence of immunity adjuvants. These immunity adjuvants are present in the natural state in microbial cell membranes in the form of molecules of the peptidoglycan type.

The vaccine of this invention is an acellular bacterial vaccine comprising:
as antigenic material, the ribosomes extracted from the bacterias against which a protection is wanted, and
as immunity adjuvant, the peptidoglycans extracted only from the cell membranes of at least one of the bacterias previously used.

The terms ribosomes and ribosomal fraction will be used synonymously and designate the ribosomes per se of bacteria which are a well known part of the bacteria, which may be contaminated by a minor part of other materials because it is well known in this field that purity of 100% cannot be reached especially on industrial scale.

The ratio between the ribosomal fraction and the membranous peptidoglycans may vary according to the nature of the bacterias used but is desirably comprised between 1/5 to 5/1 in weight and is especially 1/1,5 of ribosomal fraction/membranous fraction in weight.

The best ratio may be easily determined by methods well known in biology such as the Ouchterlany method which shows the best antibodies response by checking the precipitation zones corresponding to the presence in for example rabbit serum (treated with the vaccine) of specific antibodies desired.

The vaccines according to the present invention may be used as it is well known for other vaccines including dosage and number of unit dosage by day or by month.

The dosage of each unit dose may vary widely according to the bacterias used.

The vaccines of the present invention are particularly useful in the prevention and treatment of several conditions in the sphere of the oto-rhino-laryngology for example against rhinitis, sinusitis, pharyngitis, rhino-tracheobronchitis, asthma and otitis-pharyngitis. In this case the vaccines contain as active ingredients for example:

the ribosomal fraction of
Klebsiella pneumoniae
Diplococcus pneumoniae
Streptococcus pyogenes
Hemophilus influenzae, and
the membranal glycopeptides of
Klebsiella pneumoniae.

This kind of vaccine may be used especially under aerosol or injectable form. In this case each unit dose contains from 0.005 to 0.030 mg of ribosomal fraction and from 0.010 to 0.060 mg of membranal glycopeptides, preferably 0.020 mg and 0.030 mg respectively.

In one of the specific embodiment of the invention the vaccines for prevention and treatment of ORL disease contain as active ingredients:

| - the ribosomal fraction of | |
|---|---|
| Klebsiella pneumoniae | 30 to 40 parts in weight |
| Diplococcus pneumoniae | 25 to 35 parts in weight |
| Streptococcus pyogenes | 25 to 35 parts in weight |
| Hemophilus influenzae | 1 to 10 parts in weight, | and
membranal glycopeptides of *Klebsiella pneumoniae* in a ratio comprised between 2/1 and 1/2 in weight.

The present invention also concerns a process for preparing the vaccines stated above in which the ribosomal fraction is prepared by (a) cultivating the strain of bacterias corresponding to the ribosomal fraction desired on a growth medium, (b) decantating the bacterias cells, (c) grinding the bacterias cells in a buffer solution and eliminating the undestroyed bacterias to obtain an homogeneous cell macerate, (d) sedimenting the cells component other than ribosomal fraction, (e) sedimenting from the supernatant solution obtained the ribosomal fraction, (f) washing the ribosomal fraction with a solution containing sodium dodecyl sulphate to eliminate the protein (g) sedimenting the washed ribosomal fraction; in which the membranal glycopeptides are prepared by (a') cultivating the strain of bacterias corresponding to the ribosomal fraction desired on a growth medium, (b') decantating the bacterias cells, (c') grinding the bacterias cells in a buffer solution and eliminating the undestroyed bacterias to obtain an homogeneous macerate, (d') sedimenting the membranal fraction from the homogeneous macerate, (e') suspending the membranal fraction in saline solution and heating the suspension to destroy lytic enzyme, (f') centrifugating the suspension and washing at least one time the residue containing the membrane with saline solution containing at least one salt among NaCl and $MgCl_2$, (g') collecting the membrane and digesting the membrane, (h') sedimenting the glycopeptides thus obtained, mixing these glycopeptides and the ribosomal fraction of The bacterias are cultivated by any of the methods normally used in microbiology. So far as the types of germs treated are concerned, they will of course be governed by the required vaccine and may be determined by known method.

The cells are decanted from the growth medium in (b) by low speed centrifugation or by filtration for example on a Westfalia clarifier.

The buffer used in step (c) may be for example a tris-$MgCl_2$-NaCl buffer (pH 7) that is it contains HCl: 0,01 M
NaCl: 9 g/l
MgCl$_2$,: 6H$_2$O 0,01 M.

The homogeneous macerate of bacterias obtained in step (c) may be obtained by any known grinding method, although it is preferably obtained by subjecting a culture of germs to ultrasonic treatment at low temperature in order to macerate the germs, after which the crude macerate is centrifuged so as to sediment and eliminate the germs which have not been destroyed, this centrifuging step preferably being carried out at $10^4$ g. The supernatant phase thus obtained constitutes the homogeneous macerate used in step (d).

But if the quantity of cells is too important it is possible to grind the cell with a Manton-Gaulin grinder instead of a ultrasonic treatment.

To sediment the cell components other than ribosomal fraction in (d) it is possible to centrifuge the homogeneous cell macerate. This centrifuging step (step d) is carried out under an acceleration of from $2 \times 10^4$ to $6 \times 10^4$ g and preferably under an acceleration of $4 \times 10^4$ g over a period of about 20 minutes or $3 \times 10^4$ g over 45 minutes.

Sedimentation of step (e) may be conducted by centrifugating the solution of step (c) at very high speed, $10^5$ to $2 \times 10^5$ g and preferably around 140,000 g for 3 hours, or it is possible to precipitate the ribosomal fraction with ethanol 95% at $-20°$ C. with addition of polyethylenglycol 4000 at 100 g/l.

In this case the precipitate may be recovered by any known method such as filtration or low speed centrifugation.

The ribosomal fraction of step (e) is washed with a solvent of protein which is sodium dodecyl sulphate (SDS). This solvent may be for example the tris-HCl-MgCl$_2$-NaCl buffer cited above containing in addition 0.5% of (SDS).

After washing the ribosomal fraction is sedimented in step (g) by the same process as used in step (e).

The steps (a'), (b'), (c') and (d') may be conducted in the same manner as described for steps (a), (b), (c) and (d). The main component of cell component sedimented in step (d) is the membranes.

Extraction of the membranes from the centrifuging residue of step (d) is preferably preceded by a stage in which the lytic enzymes of the cell components present in the residue are destroyed, for example by heating the residue to $100°$ C., optionally after redissolution.

The actual extraction of the membranes from the centrifuging residue of step (d) is preferably carried out by treating the cell components of the residue, optionally after destruction of the lytic enzymes, with a saline solution, for example 1 M sodium chloride or a tris-HCl-NaCl-MgCl$_2$ buffer as cited above, either once or several times and centrifuging the suspension obtained. The supernatant phase left after this centrifuging step, which is eliminated, contains the non-membranal impurities such as proteins and nucleic acids, whilst the residue contains the membranes. This centrifuging step is preferably carried out at $2 \times 10^4$ g.

Following separation of the saline solution containing the impurities, such as proteins and nucleic acids, the membranes are digested in step (g') in the presence of proteolytic enzymes, preferably trypsin and chymotrypsin, in solution at pH 8 for 4 hours at a temperature of $37°$ C.

After digestion, homogenisation is completed by subjecting the solid digestion fraction to further ultrasonic maceration. The product thus obtained constitutes the peptidoglycanic fraction of the vaccine.

Thereafter it is sufficient to mix the ribosomal fraction obtained and the membranal peptidoglycanes in order to obtain a vaccine according to the invention.

When the ribosomal fraction or peptidoglycans used come from different strains of bacterias each strain is preferably treated independently but it is possible to treat all strains together in the process.

The active parts of the vaccine according to the invention are mixed for administration with suitable pharmaceutical carriers which are usual in the art.

DESCRIPTION OF SPECIFIC EMBODIMENTS

An ORL vaccine was prepared in the following manner:

(I) Obtaining the bacterias

The bacterial strains used are isolated from pathological samples. These germs are reactivated by passing them through laboratory animals, for example mice, and are maintained in suitable culture media. Inoculums are prepared from the microbial strains thus obtained by inoculating a liquid nutritive medium with each germ. Incubation lasts for 24 hours at $37°$ C. The inoculum is then used for inoculating a battery of fermenters intended for the preparation of vaccines. After 24 hours, culture with agitation, the medium is passed through a clarifier of the Westfalia type so as to decant the cells which are then directly washed in the clarifier with a tris-MgCl$_2$-NaCl buffer (pH 7). The germs are collected and redissolved in the same buffer at $+4°$ C. in a concentration of $10^{10}$ germs/ml.

(II) Obtaining a homogeneous cell macerate

The suspension of washed germs is macerated by ultrasonic treatment at low temperature. This treatment yields a cell macerate which still contains germs that have not been destroyed by the ultrasonic treatment. Accordingly, a first centrifuging operation at $10^4$ g is carried out for 15 minutes at $+4°$ C. so as to sediment these undestroyed germs.

The supernatant phase constitutes the homogeneous macerate of germs which is used in the main phases of the process according to the invention.

(III) Preparation of the ribosomal fraction

The various cell fractions, including the fraction described above, are separated in an MSE MK II.65 ultracentrifuge equipped with an $8 \times 50$ ml angular rotor of aluminium.

The cell macerate obtained in stage (II) is centrifuged at 40,000 g for 20 minutes at $+4°$ C. in order to sediment the cell components of the broken up germ cells except for the ribosomal fraction which remains in the supernatant phase. The supernatant phase is separated off from the centrifuging residue and is recentrifuged at 140,000 g for 3 hours at $+4°$ C. in order to sediment the ribosomal fraction with the proteins absorbed on the ribosomes.

The centrifuging residue thus obtained is then treated for 30 minutes at ambient temperature with 0.5% sodium dodecyl sulphate, this extraction enabling the proteins which are absorbed on the ribosomes to be solubilised. The dodecyl sulphate is eliminated by precipitation at $0°$ C. and centrifuging at low speed.

The supernatant phase is then centrifuged at 140,000 g for 3 hours at $+6°$ C. in order to sediment the ribosomes which are then taken up in a sterile solution of MgCl$_2$ ($10^{-2}$ N) in a physiological serum, followed by packaging in 1 ml ampoules.

(IV) Preparation of the membranal glycopeptides

This function is prepared from the residue obtained beforehand by centrifuging at 40,000 g for 20 minutes. The centrifuging residue is resuspended in a physiological serum, and the resulting suspension heated for 10 minutes to 100° C. in a boiling water bath in order to destroy the lytic enzymes. After cooling, the suspension is centrifuged for 30 minutes at 20,000 g. The residue obtained is extracted twice with 1 M NaCl in order to eliminate the proteins and the nucleic acids. The membranes are collected by centrifuging for 30 minutes at 20,000 g.

They are then digested with trypsin for 4 hours at 37° C./pH 8, and then with chymotrypsin under the same conditions.

The membranes are then collected by centrifuging at 2,000 g for 30 minutes, washed with physiological serum and then with distilled water, followed by ultrasonic disintegration for 15 minutes.

A vaccine according to the present invention is obtained by mixing the fraction thus obtained with the ribosomal fraction obtained in stage (III).

(V) Analysis

Yield of the process

The yield of the process may be evaluated by spectrophotometry.

Because the optical density of the microorganism depends on the type of microorganism treated, it is only the average yield which is quoted hereinafter.

Thus, using a 20 liter capacity fermenter, it is possible to obtain 150 ml of ribosome suspension containing $10^{10}$ germs/ml, i.e. 0.2 g of lyophilised ribosomes corresponding to $7.5 \times 10^9$ germs/mg of lyophilisate, and 50 mg of lyophilised proteoglycans.

Analysis of the products obtained

Ribosomal fractions lyophilised

Analytical Standards:

1. Physical characteristics White or creamy with freeze dried powder.
2. Solubility Very soluble in water; insoluble in alcohol, ether and chloroform.
3. Moisture content Not more than 7% when determined on a sample of about 0.1 g, accurately weighed, by the method of the French Pharmacopoeia, page II 264.
4. Assay

| (a) Total nitrogen | 9 to 11% |
|---|---|
| (b) Ribonucleic acid: as RNA | 65 to 75% |
| as phosphorus | 5.3 to 6.1% |

The antigenic ribosomes contain generally from 72 to 75% of RNA and from 20 to 28% of proteins.

The ribosomal fraction as lyophilisate is standardized assuming that it comprises 70% of RNA in weight, and the RNA is standardized using the phosphomolybdic complex.

Principle: The phosphorus content is determined by colorimentry after formation of the phosphomolybdic complex (French Pharmacopoeia (See "Technique de Laboratoire", J. Loiseleur, Book I, Sec. 2, Pgs. 983 & 984).

The result is expressed as RNA, the average phosphorus content of RNA being 8.2% (J. Biol. Chem. 216-185-193 (1955) A. M. Crestfield et al).

The RNA may also be standardized by using direct spectrophotometric examination at 256 nm by comparaison with a standard. (See "Technique de Laboratoire", J. Loiseleur, Book I, Section 2, Pages 1187-1190).

Peptidoglycan of membranous fractions

Analytical Standards:

1. Physical characteristics
   White to greyish-white freeze dried powder, with a "woolly" appearance.
2. Solubility
   A 1 in 100 aqueous solution is clear, a 1 in 10 solution is slightly opalescent; sparingly soluble in alcohol, ether and chloroform.
3. Moisture content
   Not more than 7%.
4. Assay

| (a) Phosphorus content | around 0.7 to 1% |
|---|---|
| (b) Protein | around 65 to 90% |
| (c) Total sugars | around 15 to 30% |

Phosphorus content is measured by the phosphomolybdic complex (see RNA).

Protein content is measured by colorimetry with copper sulfate (Biuret reaction). (See "Methods in Microbiology", Vol. 5B Pg. 247, Ref. Gornall et al., J. Biol. Chem. (1949) 177,751).

Total sugars is measured by colorimetry determination with anthrone reagents. (See "Methods in Enzymology", Vol. III, Pg, 84 Ref. Scott et al Analyt. Chem. (1953) 25, 1956).

Content of peptidoglycan is obtained by the sum of the protein and sugar.

The new vaccines thus obtained either by the process according to the invention or by any other process may be used in human and veterinary medicine as known vaccines for the treatment of infectious diseases.

They may be packaged and used, optionally lyophilised, in the form of injectable or drinkable ampoules or even in the form of aerosols or sprays by methods well known in the art.

SUMMARY OF CLINICAL EXPERIENCE

The vaccine used in the following tests has the following composition and is prepared according to the preferred embodiment of the process described above, this vaccine is named D 53:

| D 53 aerosol | | |
|---|---|---|
| - Ribosomal fraction (lyophilisate) obtained from associated strains: | | 4 mg |
| . ribosomes of *Klebsiella pneumoniae* | 35 parts | |
| . ribosomes of *Diplococcus pneumoniae* | 30 parts | |
| . ribosomes of *Streptococcus pyogenes* group A | 30 parts | |
| . ribosomes of *Hemophilus influenzae* | 5 parts | |
| - Membranal fraction of *Klebsiella pneumoniae* | | 6 mg |
| - Polyoxyethylened oleic glycerids | | 400 mg |
| - Eucalyptol | | 7.36 mg |
| - Dichlorodifluoromethane, for | | 10 ml |

-continued

An aerosol contains 200 doses.
D 53 injectable
Unit dose
Lyophilisate
- Ribosomal fraction (lyophilisate) obtained
  from associated strains:                    0.020 mg
    . ribosomes of Klebsiella
      pneumoniae              35 parts
    . ribosomes of Diplococcus
      pneumoniae              30 parts
    . ribosomes of Streptococcus
      pyogenes group A        30 parts
    . ribosomes of Hemophilus
      influenzae              5 parts
- Membranal fraction of Klebsiella pneumoniae   0.030 mg
- Crystalline $MgCl_2$                          0.1075 mg
- KCl                                           0.3725 mg
- Mannitol                                      11.925 mg
Solvent
- NaCl                                          2 mg
- $H_2O$, for injection, for                    0.5 ml The efficiency of the proposed vaccine has been studied on mice in comparison with an ordinary vaccine comprising the whole bacteria.

Dose of vaccine administered has been calculated in relation with the content of ribosome of bacteria of the know vaccine in order that in both injections the quantities of ribosome are equal for the same bacteria.

This known vaccine has the following composition:

| . Staphylococcus aureus | 60% | |
| . Streptococcus hemolyticus | 10% | |
| . Pneumococcus | 7.5% | whole bacterias |
| . H. influenzae | 7.5% | |
| . Klebsiella pneumoniae | 7.5% | |
| . Neisseria catarrhalis | 7.5% | |

The test is conducted in the following manner:
Day O subcutaneous injection:
  mice $R_1$ of 5 μg of D53 injectable
  mice $R_2$ of B $2.8 \times 10^{-4}$ ml of the above vaccine
Day 15 subcutaneous injection:
  mice $R_1$ of 5 μg of D53 injectable
  mice $R_2$ of $2.8 \times 10^{-4}$ ml of the above vaccine.
At day 21:
$R_1$ and $R_2$ are separated in 5 groups:
  $R_1A_3$ and $R_2A_3$ received a subcutaneous injection of Myxovirus influenza
  $R_1C_1$ and $R_2C_1$ received a subcutaneous injection of $10^4$ germs of K. pneumoniae (0.5 ml)
  $R_1C_2$ and $R_2C_2$ received a subcutaneous injection of $10^3$ germs of K. pneumoniae
  $R_1C_3$ and $R_2C_3$ received a subcutaneous injection of $10^2$ germs of K. pneumoniae
  $R_1C_4$ and $R_2C_4$ received a subcutaneous injection of 10 germs of K. pneumoniae.

The living mice are determined each days after day 21. The results are summarized in the following tables. The blank mice having only received corresponding injection of Myxovirus or K. pneumoniae.

| Lots | $J_0$ | $J+1$ | $J+2$ | $J+3$ | $J+4$ | $J+5$ | $J+6$ | $J+7$ | $J+8$ | $J+9$ |
|---|---|---|---|---|---|---|---|---|---|---|
| BLANK ($TA_3$) | 30 | 30 | 30 | 30 | 30 | 30 | 23 | 15.9* | 3.2 | 1.0 |
| ($R_1 A_3$) | 30 | 30 | 30 | 30 | 30 | 30 | 27 | 17.12 | 6.5 | 4.4 |
| ($R_2 A_3$) | 30 | 30 | 30 | 30 | 30 | 30 | 24 | 11.9 | 2.2 | 0.0 |

*1st number read at 9h00
*2nd number read at 17h00

(a) KP $10^4$ germ

| Lots | $J_0$ | $J+1$ | $J+2$ | $J+3$ | $J+4$ | $J+5$ | $J+6$ | $J+7$ |
|---|---|---|---|---|---|---|---|---|
| BLANK ($TC_1$) | 20 | 20.14 | 5.2 | 2.2 | 2 | 2 | 1 | 1 |
| ($R_1 C_1$) | 20 | 20.20 | 13.12 | 10.10 | 7 | 7 | 7 | 7 |
| ($R_2 C_1$) | 20 | 12.9 | 0 | 0 | 0 | 0 | 0 | 0 |

(b) KP $10^3$ germ ($C_2$)

| Lots | $J_0$ | $J+1$ | $J+2$ | $J+3$ | $J+4$ | $J+5$ | $J+6$ | $J+7$ | $J+8$ |
|---|---|---|---|---|---|---|---|---|---|
| BLANK ($TC_2$) | 20 | 20.20 | 12.10 | 4.4 | 3 | 3 | 3 | 3 | 3 |
| ($R_1 C_2$) | 20 | 20.20 | 19.19 | 19.10 | 18 | 18 | 18 | 18 | 18 |
| ($R_2 C_2$) | 20 | 20.19 | 15.11 | 5.5 | 4 | 4 | 4 | 4 | 4 |

(c) KP $10^2$ germ ($C_3$)

| Lots | $J_0$ | $J+1$ | $J+2$ | $J+3$ | $J+4$ | $J+5$ | $J+6$ | $J+7$ | $J+8$ |
|---|---|---|---|---|---|---|---|---|---|
| BLANK ($TC_3$) | 20 | 20.20 | 6.4 | 2.1 | 1 | 1 | 1 | 1 | 1 |
| ($R_1 C_3$) | 20 | 20.20 | 18.17 | 14.14 | 14 | 14 | 14 | 14 | 14 |
| ($R_2 C_3$) | 20 | 20.20 | 18.18 | 12.12 | 12 | 12 | 12 | 12 | 12 |

(d) KP 10 germ ($C_4$)

| Lots | $J_0$ | $J+1$ | $J+2$ | $J+3$ | $J+4$ | $J+5$ | $J+6$ | $J+7$ | $J+8$ |
|---|---|---|---|---|---|---|---|---|---|
| BLANK ($TC_4$) | 20 | 20.18 | 10.9 | 5.4 | 4 | 4 | 4 | 4 | 4 |
| ($R_1 C_4$) | 20 | 20.20 | 20.20 | 20.20 | 20 | 20 | 20 | 20 | 20 |
| ($R_2 C_4$) | 20 | 20.16 | 6.2 | 0 | 0 | 0 | 0 | 0 | 0 |

The above tests indicate that the vaccine according to the invention is far more active than the known vaccine as standard.

D 53 aerosol has been used in several clinical trials carried out in France. The following summary of the scope of these trials provides an indication of the clinical experience gained with the product to date.
Number of trials: 4
Number of patients treated with D 53 aerosol: 144 (including 40 children aged 5-15 years)
Number of patients abandoning treatment: 2 (no reasons given)

| Main indications: | Rhinitis | Rhino-tracheo-bronchitis |
|---|---|---|
| | Sinusitis | Asthma |
| | Pharyngitis | Otitis-pharyngitis |

Dosage employed:

D 53 aerosol is provided with attachments which permit administration both orally and into the nasal sinuses. In all the trials dosage involved the use of both routes, as detailed below.

In two of the trials dosage was based on the following scheme:

one metered aerosol dose orally and in each nostril, three times a week for 5 weeks.

After a gap of 1 month, three further doses over a 1 week period. (93 patients)

In the other two trials dosage was: one metered aerosol dose orally and in each nostril three times a day for 3 weeks. (51 patients)

Results:

In one of the trials the aerosol dosage was augmented with periodic administration of an injection presentation of the D 53 formula.

One of the other trials involved healthy volunteers where the prophylactic effect of D 53 was being investigated.

For only two of the trials, involving 51 patients, is it possible to give specific clinical results for D 53 aerosol. In 34 of these patients the results were considered to be good or very good, i.e. 65%.

Immunologically it was shown that there was a highly significant increase in serum IGA and IGM in one trial, IGA only in the two other trials, and IGM only in the fourth trial.

Two of the trials were conducted on a double-blind basis, using a similar aerosol product for reference. The control preparation contained a freeze dried extract from a suspension containing the following bacterial strains

| | |
|---|---|
| Staph. aureus | Strep. faecalis |
| Pseudomonas aeruginosa | Proteus vulgaris |
| E. coli | Neisseria catarrhalis |
| Pneumococcus | H. influenzae |
| Strep. pyogenes | Klebsiella pneumoniae |

There was no indication whether this extract was activated by an adjuvant.

In both trials where this product was used as a comparison D 53 gave significantly better results.

Tolerance:

No untoward reactions occurred in any of the trials, the only side effect of any kind being mild pharyngeal irritation in a few patients. The general tolerance was excellent.

Conclusions:

D 53 aerosol was shown to be effective in the treatment of several conditions in the sphere of otorhinolaryngology. At dosages of three times a week or three times a day, each dose consisting of oral inhalation and nasal administration, no side effects of any consequence resulted.

What is claimed is:

1. A process for the preparation of an acellular vaccine comprising (1) at least one ribosome extracted from pathogenic bacteria against which protection is desired, said ribosome functioning as an antigenic material and (2) peptidoglycans extracted only from the cell membranes of at least one of the bacteria used in (1), said process comprising
   (a) extracting ribosomes from said bacteria by
      (I) cultivating the strain of bacteria corresponding to the desired ribosomal fraction on a growth medium;
      (II) decanting the bacterial cells of (I);
      (III) grinding said bacterial cells in a buffer solution and eliminating the undestroyed bacteria to form an homogeneous cell macerate;
      (IV) ultracentrifuging the homogeneous macerate of said bacteria under an acceleration from about $2 \times 10^4$ to $6 \times 10^4$ g to form (i) a supernatant phase containing the ribosomes on which impurities of the protein-type are absorbed and (ii) a residue containing all other components;
      (V) separating and supernatant phase from said residue;
      (VI) ultracentrifuging the separated supernatant phase under an acceleration from about $10^5$ to about $2 \times 10^5$ g to form a centrifuged residue;
      (VII) treating said centrifuged residue with a solution of sodium dodecylsulfate;
      (VIII) precipitating sodium dodecylsulfate at low temperature; and
      (IX) ultracentrifuging the resulting supernatant solution under an acceleration from about $10^5$ to about $2 \times 10^5$ g, thus forming a residue containing purified ribosomes;
   (b) forming peptidoglycans from the cell membranes of said bacteria by
      (I) treating the residue of step (a) (IV) (ii) with a saline solution
      (II) centrifuging the resulting saline solution-residue mixture to extract the bacterial cell membranes;
      (III) digesting the extracted membranes with a proteolytic enzyme to separate membranal glycopeptides, and (IV) centrifuging the membranal glycopeptides, and
   (c) mixing the purified ribosomes of (a) (IX) and the membranal glycopeptides of (b) (IV).

2. The process of claim 1, further comprising heating the centrifuged residue of (a) (IV) (I) to 100° C.

3. The process of claim 2 wherein said saline solution of (b) (I) is a 1 M NaCl solution.

4. The process of claim 3 wherein said proteolytic enzyme of (b) (III) is trypsin or chymotrypsin.

5. The process of claim 1 wherein the bacteria are selected from the group consisting of
   Klebsiella pneumoniae,
   Diplococcus pneumoniae,
   Streptococcus pyogenes, and
   Hemophilus influenzae.

* * * * *